| [19] | United States Patent | [11] | Patent Number: | 5,015,715 |
| Divers et al. | | [45] | Date of Patent: | May 14, 1991 |

[54] METHOD FOR BONDING AN ANALYTE-SENSITIVE DYE COMPOUND TO AN ADDITION-CURE SILICONE

[75] Inventors: George A. Divers, San Diego; Henry K. Hui, Laguna Niguel, both of Calif.

[73] Assignee: Puritan-Bennett Corporation, Carlsbad, Calif.

[21] Appl. No.: 394,637

[22] Filed: Aug. 16, 1989

[51] Int. Cl.$^5$ ............................................. C08G 77/06
[52] U.S. Cl. ........................................ 528/15; 528/10; 528/31; 528/32; 528/30; 528/43
[58] Field of Search ................ 538/43, 15, 10, 31, 538/32, 30

[56] References Cited

U.S. PATENT DOCUMENTS

| 3,612,866 | 10/1971 | Stevens | 250/71 |
| 3,725,658 | 4/1973 | Stanley et al. | 250/71 |
| 4,194,877 | 3/1980 | Peterson | 8/4 |
| 4,468,229 | 8/1984 | Su | 8/507 |
| 4,657,736 | 4/1987 | Marsoner et al. | 422/56 |
| 4,712,865 | 12/1987 | Hsu et al. | 328/43 |
| 4,714,770 | 12/1987 | Hsu et al. | 528/43 |
| 4,746,751 | 5/1988 | Oviatt, Jr. et al. | 556/456 |
| 4,775,514 | 10/1988 | Barnikol et al. | 422/68 |
| 4,916,169 | 4/1990 | Boardman et al. | 528/15 |

FOREIGN PATENT DOCUMENTS

| 0283206 | 9/1988 | European Pat. Off. |
| 106086 | 5/1974 | Fed. Rep. of Germany |
| WO88/05533 | 7/1988 | PCT Int'l Appl. |
| 2132348A | 7/1984 | United Kingdom |

OTHER PUBLICATIONS

Hui, Henry K., et al., An Accurate, Low-Cost, Easily-Manufacturable Oxygen Sensor, 1989.

*Primary Examiner*—Melvyn I. Marquis
*Attorney, Agent, or Firm*—Fulwider, Patton, Lee & Utecht

[57] ABSTRACT

A method for covalently bonding an analyte sensitive dye compound to an additon-cure silicone is disclosed. The method includes a first step of functionalizing the dye compound to provide a linker arm with an isolated multiple bond. A second step includes hydrosilylating the functionalized dye with polymethylhydrosiloxane. The resulting compound is cross-linked with vinyl-terminated polysiloxane in a third and final step.

17 Claims, No Drawings

METHOD FOR BONDING AN ANALYTE-SENSITIVE DYE COMPOUND TO AN ADDITION-CURE SILICONE

BACKGROUND OF THE INVENTION

1. Field of the Invention

The present invention is generally related to the measurement of concentrations of analytes in a fluid or gaseous mixture, and more specifically, to a method for making an improved oxygen-sensing optode in which the indicator substance is covalently bonded onto a matrix.

2. Description of the Prior Art

Fiber-optic based oxygen sensing apparatus have proliferated over the years due to their numerous applications in the medical, chemical and environmental fields. Many oxygen sensors rely on the phenomenon of fluorescence quenching as a means for determining the presence of oxygen in a liquid or gaseous mixture. Fluorescence quenching has been a widely used approach for such devices due to the high sensitivity that can be achieved. Systems and instruments implementing fluorescence quenching techniques utilize an encapsulated oxygen-quenchable fluorescence dye that is placed within a gas permeable matrix usually made from a polymer or similar substance. The dye/matrix, called a sensor element or optode, can be applied to the tip of an optical fiber using well-known techniques in the art. A light source with appropriate filtering system provides a select wavelength of light which propagates down the optical fiber and excites the dye. The fluorescence signal, induced by the excitation energy, travels back down the same optical fiber and is collected by a photodetector. The intensity of the fluorescence of the dye, which is a function of the oxygen level in the sample, can be transduced into a partial pressure of oxygen.

While many sensor elements have been developed for use with oxygen measuring devices, there are inherent problems associated with them that are detrimental to the accuracy of the measurements. For example, it is sometimes a difficult task to immobilize the fluorescent dye in a gas permeable matrix because of the chemical and/or physical incompatibility between the dye and matrix. Many of the more widely used oxygen fluorescent dyes are polynuclear aromatic compounds which, because of their high degree of symmetry, usually have low solubility in organic materials. As a result, the fluorescent dyes have a tendency to leach through the permeable matrix into the solution or gas mixture that is being tested.

Various approaches for creating an operable sensor element include absorbing the dye on inorganic or organic solid supports and dispersing the dye in the matrix by way of organic solvents. Many of these techniques still have serious drawbacks if the dye is chemically incompatible with the polymer matrix. These dyes still have a tendency to leach out, particularly when in contact with a sample that includes a substance that has similar properties as the dye/polymer matrix. Unfortunately, such substances include blood proteins and many organic solvents, which are often the samples being tested. As a result of the leaching of the dye during use, the sensing element may have to be continuously replaced to ensure the accuracy of oxygen measurements. Moreover, symmetrical dye molecules that are free to move within a polymer matrix tend to agglomerate which results in changes in fluorescent properties.

Accordingly, those concerned with the development and use of oxygen sensing devices have long recognized the need for an improved method for creating a sensor element that will not leach when placed in the sample solution or during storage and will not suffer dye agglomeration over time. Preferably, the improved method should produce a dye/matrix that can be readily affixed to the end of an optical fiber or other similar device in a single step. Moreover, the sensor made according to the method should be relatively inexpensive to manufacture and should provide accurate oxygen measurements.

SUMMARY OF THE INVENTION

The present invention provides a method by which a sensor element can be manufactured in which a polynuclear aromatic dye compound is covalently bonded to an addition-cure silicone. The method is a three-part process which first requires the polynuclear aromatic dye to be functionalized to provide a linker arm with isolated multiple bonds to lower the degree of symmetry of the dye and thereby increase its solubility when placed in a polymer matrix. The next step requires the hydrosilylation of the functionalized dye with polymethylhydrosiloxane to form a compound that can be later cross-linked with vinyl-terminated polysiloxane in a final step.

The dye contained in the polysiloxane of the present invention exhibits high gas permeability and sensitive oxygen quenching fluorescence which make it extremely advantageous for use in optical systems that measure oxygen gas. The dye/matrix structure results in a formation of a cross-linked silicone rubber with the dye covalently bonded to it. The cross-linked silicone can take on different characteristics by changing substitutions on the vinyl-terminated polysiloxanes. Viscosity and physical strength of the silicone can also be varied by changing the molecular weight of the polysiloxane. As a result, the dye is less susceptible to leaching or agglomeration. A sensor element made in accordance with the method of the present invention can be more accurate than prior art sensors and can be used over and over again.

DETAILED DESCRIPTION OF THE INVENTION

The present invention is embodied in a method for bonding an oxygen-sensitive indicator substance to an addition-cure silicone to form a sensor element that is particularly resistant to leaching of the indicator substance through the polymer matrix. The oxygen-sensitive fluorescent indicator substance is usually a polynuclear aromatic compound which is capable of fluorescent quenching. The matrix is an addition-cure silicone which provides a permeable substance that is hydrophobic and prevents leaching of the indicator dye since the dye is bonded to the silicone.

The method by which the polynuclear aromatic compound is bonded to the addition-cure compound can be divided into the following three processes:

First, dye indicator is functionalized to provide a linker arm with an isolated multiple bond.

Second, the functionalized dye indicator is hydrosilated with polymethylhydrosiloxane to form an intermediate compound.

Lastly, this intermediate compound is crosslinked with vinyl-terminated polysiloxane to form the dye/matrix.

The polynuclear aromatic dye compound has a high degree of symmetry that results in its low solubility in organic materials. As a result, it must be first functionalized to lower its degree of symmetry, thereby increasing its solubility in the polymer matrix. The functionalization step provides a linker arm with a terminal multiple bond. This linker arm is necessary since it will help minimize steric interaction between the dye and the polymer. Moreover, the linker arm provides a means to locate the multiple bond remote from the conjugated aromatic systems.

The linker arm may consist of essentially a hydrocarbon chain or it may contain heteroatoms such as nitrogen, sulfur, phosphorus, or silicon. The isolated multiple bond can be any one from a group that includes a carbon-carbon, a carbon-oxygen, a carbon-nitrogen or a nitrogen-nitrogen bond. Any chemical method which results in the addition of a linker arm and an isolated multiple bond to the dye molecule is contemplated by the present invention and falls within the spirit and scope of the invention.

The polynuclear dye compound used with the method of the present invention includes, but is not limited to, perylene, benzoperylene, coronene, decacyclene and still others. The chain length of the linker arm can range from n=1 to 22. The multiple bonds can be a double or triple bond.

The following examples are included for further understanding of the invention. The first two examples show two methods for completing the functionalization step. It should be understood that these examples are included for the purpose of illustration but in no way are intended to limit the scope of the present invention.

A FIRST EXAMPLE DEMONSTRATING THE FUNCTIONALIZATION STEP

In order to demonstrate the first step of the method of the present invention, a polynuclear aromatic compound, namely benzoperylene, was formylated with α, α- dichloromethyl methyl ether in a Friedel-Crafts acylation reaction. The yield from this mixture was 1-benzoperylene carboxaldehyde as is shown in the following equation:

EQ. 1

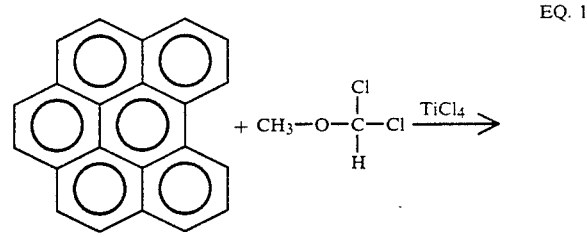

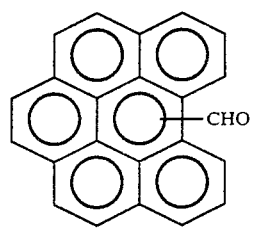

The 1-benzoperylene carboxaldehyde was reduced with LiAlH$_4$ which resulted in the formation of 1-benzoperylene methyl alcohol. Equation 2 describes this reaction and is shown below:

EQ. 2

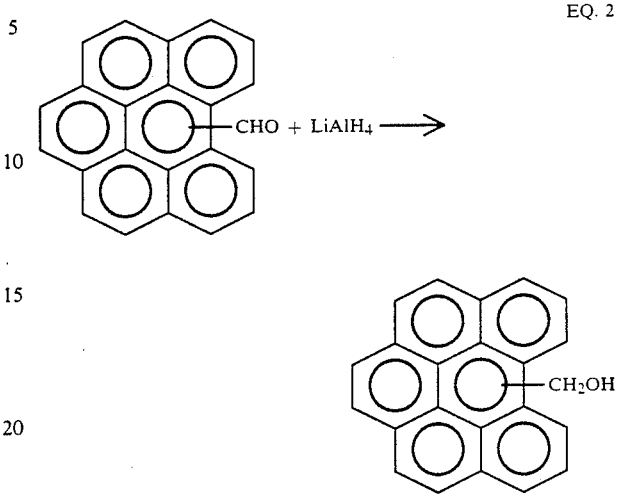

This methyl alcohol was treated with 1-bromoctene in DMSO/NaOH to form 8-octenyl benzoperylene methyl ether. Equation 3 which describes this reaction appears below:

EQ. 3

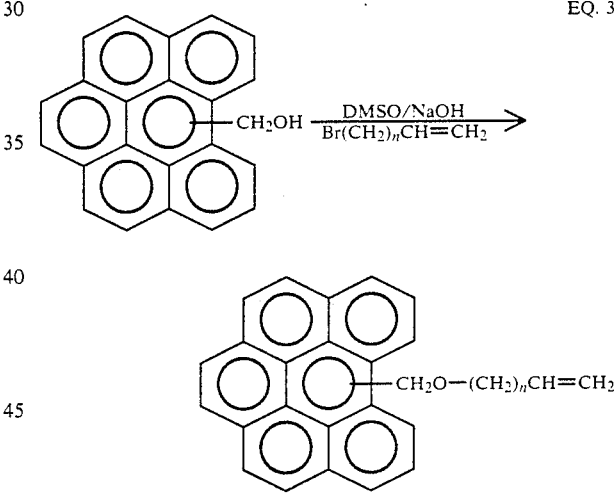

where n = 1, 2, 4, 6

Analogous reactions with 3-propenyl bromide, 4-butenyl bromide and 6-hexenyl bromide, shown in Equation 3 above, provide corresponding ethers.

A SECOND EXAMPLE DEMONSTRATING THE FUNCTIONALIZATION STEP

In order to further demonstrate the first step of the present invention, benzoperylene was again chosen as the polynuclear aromatic compound. Butyl lithium/T-MEDA was added to the benzoperylene in tetrahydrofuran at room temperature to generate benzoperylene carbanion. This carbanion was quenched with 3-propenyl bromide, 4-butenyl bromide, 6-hexenyl bromide, and 8-octenyl bromide resulting in the formation of substituted benzoperylene with different hydrocarbon chain lengths. Equation 4 below describes this reaction:

EQ. 4

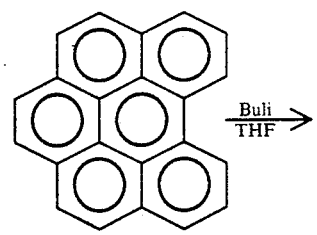
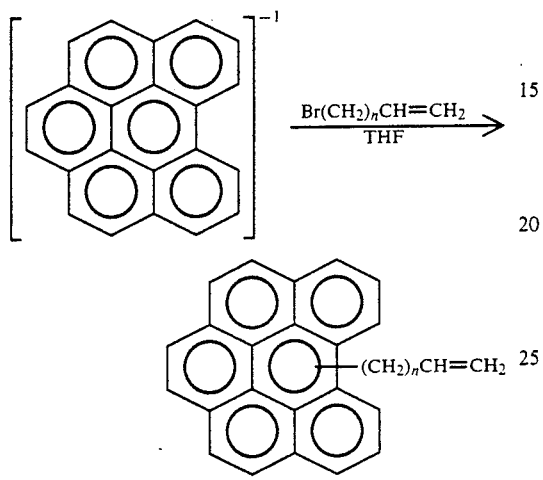

where n = 1, 2, 4, 6

The second step of the method, the hydrosilylation of the functionalized polynuclear aromatic compound with polymethylhydrosiloxane, can be performed by several well known methods. The following formula discloses a typical polymethylhydrosiloxane:

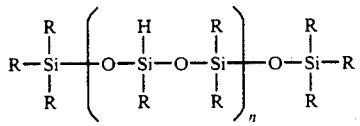

Where R = H, $CH_3$, $CH_2CH_2CF_3$, $CH_2(CH_2)_nCH_3$ and phenyl

Polymethylhydrosiloxanes are available with different degrees of Si—H substitutions and different R group functionalities. The amount of Si—H substitutions will determine the number of dye molecules that can be bonded to the polymer. The type of R group on the polymethylhydrosiloxane will determine the refractive index of the polymer and the solubility of the dye molecule in the silicone reaction mixture. The higher the solubility of the dye in the polymer, the more likely the dye will bond.

AN EXAMPLE DEMONSTRATING THE HYDROSILYLATION STEP

In order to better understand the hydrosilylation step of the present invention, a reaction mixture which consists of 15 mg of 8-octenyl coronene ($4 \times 10^{-2}$ mmol), 1 g of polymethylhydrosiloxane (50–55% SiH, 8 mmol) and 1 drop of 10% platinic acid was heated to 120° C. under an inert atmosphere for 16 hours (See EQ 5 below) with the solid dye compound slowly solubilizing into the polymer. At the end of the reaction period, the dye-bound silicone liquid was filtered through Celite to remove impurities.

EQ. 5

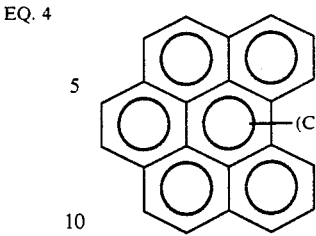

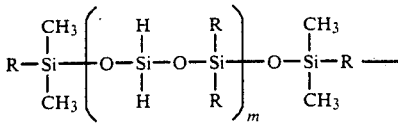

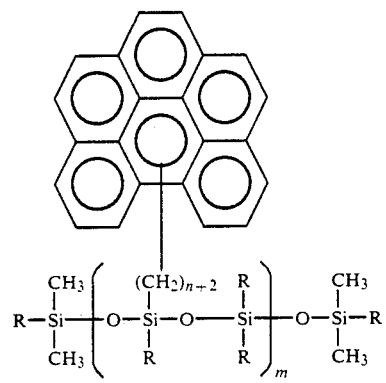

This scheme provides flexibility to vary the dye concentration by changing the percent Si—H substitution on the polymethylhydrosiloxane. The refractive index and physical strength of the polymer can be changed by varying R. The dye/polymer is extremely stable when stored in a dark and cool environment.

The final step of the method, the cross-linking of the polysiloxane with the hydrosilylated polynuclear aromatic compound, can also be accomplished using known techniques in the art. For example, a mixture of dye/polyhydrosiloxane and vinyl-terminated polysiloxane when heated in the presence of platinum catalyst, results in the formation of a cross-linked silicone rubber with dye covalently bonded to it. The cross-linked silicone can take on different characteristics by changing substitutions on the vinyl-terminated polysiloxanes. Viscosity and physical strength of the silicone can also be varied by changing the molecular weight of the polysiloxane.

AN EXAMPLE DEMONSTRATING THE CROSS-LINKING STEP

In this final step, 10 mg of dye/polyhydrosiloxane and 50 mg of vinyl-terminated polymethylphenylsiloxane with 5 ppm of platinum catalyst were mixed in an aluminum dish. The silicone mixture was degassed under a vacuum and was applied to the optical fiber. The chemistry was cured by heating the fiber tip in an oven at 100° C. for 1 hour.

The optical fiber containing the cured matrix was connected to the instrument. The fiber tip was placed in a saline solution and 7% $O_2$ gas was introduced. When the chemistry was irradiated with 380 nm light, the emission at 440 nm yielded a normalized voltage of 2.857 V. When the concentration of O2 was increased to 20%, the resulting voltage was 1.934 V. A voltage of 2.852 V was registered when the $O_2$ level was reverted back to 7% showing reversibility and no hysteresis. The sensing tip was also placed in media such as methylene chloride, methyl alcohol, isopropyl alcohol, silicone liquids, and bovine blood. No noticeable drop in signal was observed.

From the above examples, it is evident that the present invention provides a chemical method for covalently bonding a polynuclear aromatic dye to an addition-cure silicone. While a particular form of a method performed in accordance with the present invention has been described, it will also become apparent to those skilled in the art that various modifications may be made without departing from the spirit and scope of the invention. Accordingly, it is not intended that the invention be limited, except as by the appended claims.

We claim:

1. A method for bonding an analyte-sensitive indicator substance to addition-cure silicone to form a sensor element compressing the steps of:

functionalizing the analyte-sensitive indicator substance to obtain a linker arm with an isolated multiple bond;

hydrosilylating the functionalized indicator substance with a polymethylhydrosiloxane; and cross-linking the resulting compound with vinyl-terminated polysiloxane.

2. The method of claim 1 wherein the indicator substance is a polynuclear aromatic compound.

3. The method of claim 1 wherein the polymethylhydrosiloxane has the following formula:

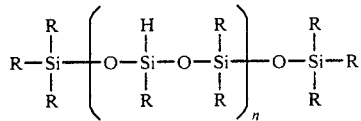

where n is an integer of from 1 to 500, and
R is independently selected from the group consisting essentially of $H, CH_3$, $CH_2CH_2CF_3$, $CH_2(CH_2)_nCH_3$ and phenyl.

4. The method of claim 1 further comprising the step of:

adding a catalyst to the compound during the cross-linking step.

5. The method of claim 1 wherein the isolated multiple bond is a carbon-carbon bond.

6. The method of claim 1 wherein the isolated multiple bond is select from a group consisting of carbon-oxygen, carbon-carbon, carbon-nitrogen and nitrogen-nitrogen.

7. The method of claim 2 wherein the polynuclear aromatic compound is selected from a group consisting of perylene, benzoperylene, coronene and decacyclene.

8. The method of claim 1 wherein the indicator substance is a polynuclear aromatic compound and the functionalization step comprises the following steps:

formylating the polynuclear aromatic compound with dichloromethyl methyl ether in a Friedel-Crafts acylation reaction, reducing the formed aldehyde with $LiAlH_4$ to form a polynuclear aromatic methyl alcohol, and treating the polynuclear aromatic methyl alcohol with the species selected from a group comprising 3-propenyl bromide, 4-butenyl bromide, 6-hexenyl bromide and 8-octenyl bromide in DMSO/NaOH to form the corresponding ethers.

9. The method of claim 1 wherein the indicator substance is a polynuclear aromatic compound and the functionalization step comprises the following steps:

adding butyl lithium/tetramethylethylenediamine to the polynuclear aromatic compound in tetrahydrofuran at room temperature to generate a polynuclear aromatic anion; and quenching the polynuclear aromatic anion with the species selected from a group comprising 3-propenyl bromide, 4-butenyl bromide, 6-hexenyl bromide and 8-octenyl bromide.

10. The method of claim 8 wherein the polynuclear aromatic compound is selected from a group consisting of benzoperylene, perylene, coronene and decacyclene.

11. The method of claim 9 wherein the polynuclear aromatic compound is selected from the group consisting of benzoperylene, perylene, coronene, and decacyclene.

12. The method of claim 1 wherein the linker arm contains a heteroatom.

13. The method of claim 1 wherein the functionalization step is performed by adding a linker molecule.

14. The method of claim 1 wherein the molar concentration of the Si—H component of the polymethylhydrosiloxane can be varied.

15. The method of claim 1 wherein the analyte is oxygen.

16. A sensor element manufactured in accordance with the method of claim 1.

17. The method of claim 4, further comprising the step of:

adding a platinum catalyst to the compound during the cross-linking step.

* * * * *